(12) United States Patent
Gehrig et al.

(10) Patent No.: US 9,013,194 B2
(45) Date of Patent: Apr. 21, 2015

(54) CAPACITIVE ANALYSIS OF A MOVING TEST MATERIAL

(75) Inventors: Reto Gehrig, Degersheim (CH); Karl Bleisch, Uster (CH); Beat Koller, Uster (CH)

(73) Assignee: Uster Technologies AG, Uster (CH)

( * ) Notice: Subject to any disclaimer, the term of this patent is extended or adjusted under 35 U.S.C. 154(b) by 0 days.

(21) Appl. No.: 14/004,006

(22) PCT Filed: Dec. 14, 2011

(86) PCT No.: PCT/CH2011/000297
§ 371 (c)(1),
(2), (4) Date: Sep. 9, 2013

(87) PCT Pub. No.: WO2012/122661
PCT Pub. Date: Sep. 20, 2012

(65) Prior Publication Data
US 2013/0342225 A1    Dec. 26, 2013

(30) Foreign Application Priority Data
Mar. 11, 2011   (CH) .......................................... 418/11

(51) Int. Cl.
*G01R 27/26* (2006.01)
*G01B 7/16* (2006.01)
*G01D 5/24* (2006.01)
(Continued)

(52) U.S. Cl.
CPC .............. *G01R 27/2605* (2013.01); *G01D 5/24* (2013.01); *G01N 27/226* (2013.01); *G01N 27/225* (2013.01); *G01B 7/16* (2013.01); *G01N 27/221* (2013.01); *G01N 27/22* (2013.01); *G06K 9/0002* (2013.01); *G01L 9/12* (2013.01); *G01C 19/5719* (2013.01); *G01L 1/14* (2013.01); *G01N 27/223* (2013.01); *G01N 33/365* (2013.01); *G01N 27/228* (2013.01)

(58) Field of Classification Search
CPC ... G01N 27/22; G01N 27/221; G01N 27/223; G01N 27/225; G01N 27/226; G01N 27/228; G01N 33/365; G01C 19/5719; G01D 5/24; G06K 9/0002; G01L 9/12; G01L 1/14; G01L 1/142; G01B 7/16; G01B 7/22; G01R 27/2605
USPC ......... 324/686, 684, 658, 649, 600, 663, 664, 324/665, 674, 681; 73/780, 774, 763, 760, 73/862.337, 862.626, 514.32, 335.04
See application file for complete search history.

(56) References Cited

U.S. PATENT DOCUMENTS

| | | | |
|---|---|---|---|
| 3,731,069 A | 5/1973 | Goto et al. | |
| 6,072,319 A | 6/2000 | Schoni | |
| 6,346,819 B1 | 2/2002 | Joss et al. | |
| 6,369,588 B1 | 4/2002 | Sleefe et al. | |
| 7,712,373 B2 * | 5/2010 | Nagle et al. | ..................... 73/780 |

(Continued)

FOREIGN PATENT DOCUMENTS

| | | |
|---|---|---|
| WO | 2005033697 | 4/2005 |
| WO | 2008128363 | 10/2008 |

*Primary Examiner* — Hoai-An D Nguyen
(74) *Attorney, Agent, or Firm* — Luedeka Neely Group, P.C.; Rick Barnes (57) ABSTRACT

The capacitive measuring circuit for a moved elongated test material contains at least two measuring capacitors, each of which is configured for receiving the test material. It further contains electrically actuatable selection means, by means of which one of the measuring capacitors can be selected in such a way that only the selected measuring capacitor contributes to the measurement, whereas the other measuring capacitors do not. As a result, the total capacitance of the measuring circuit is reduced and its sensitivity is increased.

15 Claims, 4 Drawing Sheets

(51) Int. Cl.
*G01N 33/36* (2006.01)
*G01N 27/22* (2006.01)
*G06K 9/00* (2006.01)
*G01L 9/12* (2006.01)
*G01C 19/5719* (2012.01)
*G01L 1/14* (2006.01)

(56) References Cited

U.S. PATENT DOCUMENTS

2011/0181304 A1 7/2011 Gehrig
2011/0193572 A1 8/2011 Gehrig
2011/0254567 A1 10/2011 Gehrig et al.

* cited by examiner

CAPACITIVE ANALYSIS OF A MOVING TEST MATERIAL

BACKGROUND

The present invention relates to a device and a method for the capacitive analysis of a moving strand-like, preferably textile, test material according to the preamble of the independent claims. It is preferably, but not exclusively, used in the off-line measurement of mass unevenness of yarn, roving or sliver, as carried out on textile laboratory test instruments.

EP-0'924'518 A1 discloses a device for the capacitive measurement of the properties of a textile product such as a sliver, roving or yarn. For the purpose of better understanding of this state of the art, a number of aspects of EP-0'924'518 A1 which are in connection with the present invention will be illustrated in the enclosed FIGS. 1 and 2.

Figure 1:
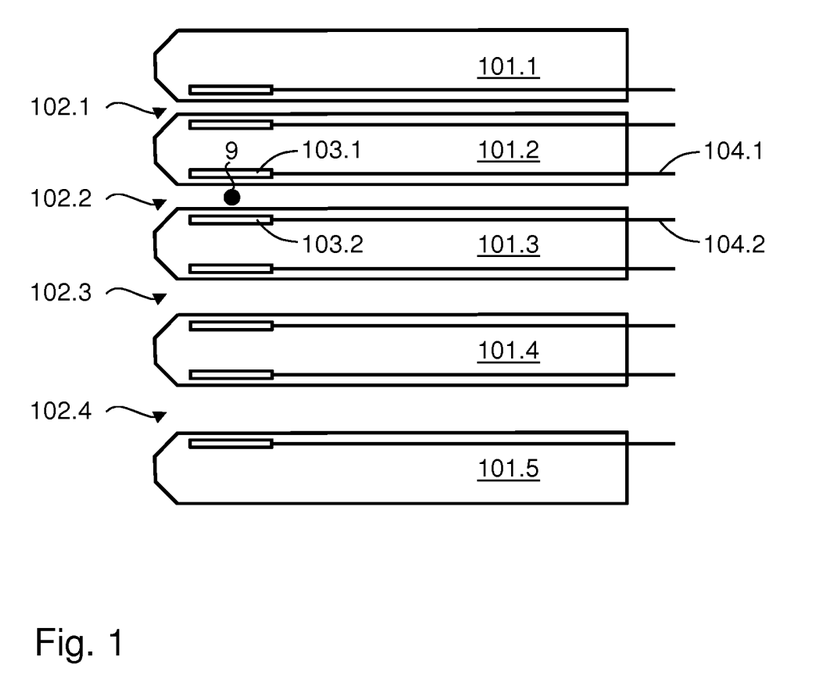
FIG. 1 shows parts of an device in accordance with the invention, which also known from EP-0'924'518 A1.

The illustration of FIG. 1 corresponds to that of FIG. 13 of EP-0'924'518 A1, and shows five carrier plates 101.1-101.5 which form four lead-through openings or measuring gaps 102.1-102.4. The test material 9 is guided through one of the measuring gaps 102.2. Since the carrier plates 101.1-101.5 are situated substantially parallel next to one another, the test material 9 can only be inserted precisely into one measuring gap 102.2 and can be moved through said gap along its longitudinal axis. The measuring gaps 102.1-102.4 each comprise one electrode 103.1, 103.2 of a measuring capacitor and one respective electrode (not shown in FIG. 1) of a compensation capacitor in or on its two side walls between which the product 9 can be guided. Disturbing influences such as local changes in humidity or deformations in the capacitor geometry can be compensated effectively by means of the compensation capacitor whose capacitance is as large as that of the measuring capacitor. Electrical lines 104.1, 104.2 connect the measuring and compensation capacitors to a measuring circuit (not shown in FIG. 1). The measuring gaps 102.1-102.4 have different widths, so that the test material 9, depending on its cross-section, can be measured in a measuring gap 102.2 with suitable width. Principally, it is desired to select the measuring gap width in such a way that on the one hand the test material 9 can be guided through the measuring gap 102.2 without touching its walls, but that on the other hand the measuring gap 102.2 is not much wider than the cross-section of the test material 9. The larger the fraction of the measuring gap 102.2 that is filled out by the test material, the higher the sensitivity of the device relating to the properties of the test material 9 changing during the measurement, e.g. mass unevenness. The widths of the measuring gap 102.1-102.4 can lie in the range of between 0.1 mm and 10 mm, for example.

Figure 2:
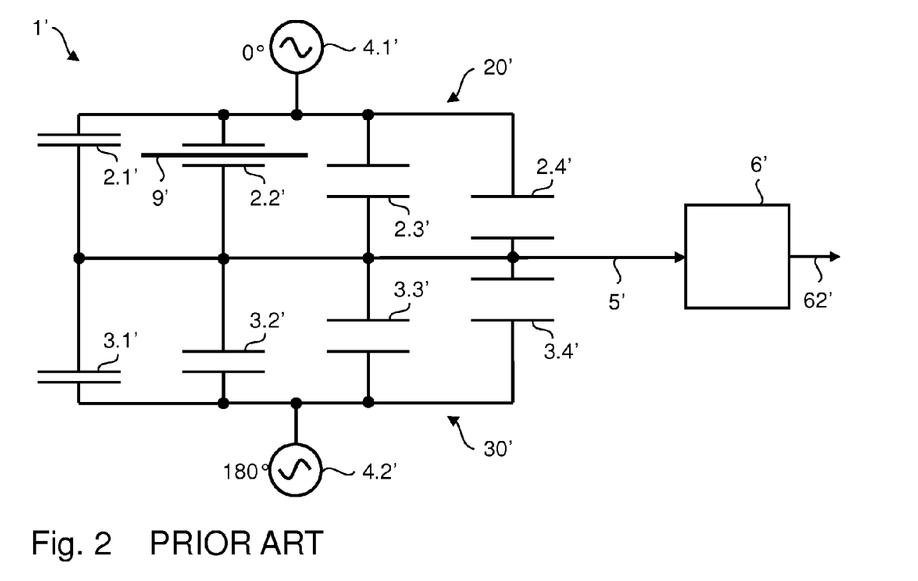
FIG. 2 shows a capacitive measuring circuit known from EP-0'924'518 A1.

FIG. 2, which substantially corresponds to FIG. 2 of EP-0'924'518 A1, shows a measuring circuit 1' configured as a half measuring bridge with four measuring capacitors 2.1'-2.4' and four associated compensation capacitors 3.1'-3.4'. The measuring capacitors 2.1'-2.4' are connected in parallel with respect to each other and form a first half bridge branch 20', whereas the compensation capacitors 3.1'-3.4', which are also connected in parallel with respect to each other, form a second half bridge branch 30'. The two half bridge branches 20', 30' are connected in series with respect to each other, and an output signal is tapped between them on a line 5'. Equally large alternating voltages in anti-phase are applied to the two half bridge branches 20', 30' by alternating voltage generators 4.1', 4.2'. When the half measuring bridge 1' has been calibrated and no test material 9' is situated in one of the measuring capacitors 2.1'-2.4', the two half bridge branches 20', 30' have equally large total capacitances; the output signal is therefore zero. If on the other hand a test material 9' is inserted into a measuring gap of a measuring capacitor 2.2', it influences the capacitance of the measuring capacitor 2.2'. The change in capacitance of the respective measuring capacitor 2.2' that is generated in this manner disturbs the equilibrium between the measuring capacitors 2.1'-2.4' and the compensation capacitors 3.1'-3.4', so that an alternating voltage is obtained as an output signal whose amplitude is proportional to the mass of the test material 9' between the measuring electrodes. This output signal is processed in a signal processing unit 6', e.g. it is amplified, filtered and/or converted, and evaluated as a measure for the mass per unit of length of the test material 9'.

Devices are known from WO-2005/033697 A1 or U.S. Pat. No. 3,731,069 A which comprise several identical lead-through openings with identical measuring capacitors. In the respective measuring methods, several yarns are tested simultaneously, i.e., one yarn in each lead-through opening. In this process, the capacitive measuring signals of the measuring capacitors are supplied serially or sequentially to a common electronic evaluation system. U.S. Pat. No. 6,369,588 B1 discloses a device and a method for the capacitive analysis of a fabric. The fabric moved along its longitudinal direction is scanned over its entire width by several capacitive sensors. Signals of the capacitive sensors are supplied serially to a common microprocessor for evaluation.

WO-2008/128363 A1 discloses a measuring capacitor for a yarn which comprises two measurement electrodes which are arranged behind one another in the direction of movement of the yarn. The effective length of the measuring field can be varied in that short yarn defects are detected with only one of the two measurement electrodes and long yarn defects with both together. The two measurement electrodes can also be used for measuring the speed or length by means of runtime correlation.

SUMMARY

It is an object of the present invention to improve the device and the measuring method according to EP-0'924'518 A1. In particular, the measuring sensitivity shall be increased and the loading capacity decreased. The number of the lead-through openings shall be reduced and simultaneously the possibility for measuring very thin test materials shall be offered. The signal-to-noise ratio shall be increased. The operating voltage of the measuring circuit shall be reduced and thus the consumed electrical power shall be decreased. The production costs shall be reduced by using more cost-effective components. The effects of dust accumulation in the lead-through openings shall be reduced.

These and other objects are achieved by the device in accordance with the invention and the method in accordance with the invention, as defined in the independent claims. Advantageous embodiments are contained in the dependent claims.

The invention is based on the idea that only the one measuring capacitor is considered in the measurement in which the test material is currently situated, whereas all other measuring capacitors are disregarded. As a result, the total capacitance of the measuring circuit is reduced and its sensitivity is increased. Calculations show that in the case of a number of n measuring capacitors (wherein n≥2 is a positive integer) and under the assumption that all capacitors have the same capacitance, the sensitivity of the measuring circuit in accordance with the invention in comparison with the known measuring circuit can be increased theoretically by the factor n. This represents a very considerable improvement. The advantage of higher sensitivity is gained by the disadvantage of a slightly more complex configuration of the measuring circuit. For the selection of the measuring capacitor to be considered it is necessary to provide electrically actuatable selection means such as a multiplexer or several switches.

The device in accordance with the invention for the capacitive analysis of a moved strand-like test material comprises at least two lead-through openings with different geometrical masses, which are mutually arranged in such a way that the test material is movable along its longitudinal axis through precisely one of the at least two lead-through openings. Furthermore, the device comprises a conveying mechanism for conveying precisely one test material through precisely one selected of the at least two lead-through openings. Finally, the device is provided with a capacitive measuring circuit. The measuring circuit contains at least two measuring capacitors, of which each is configured for accommodating the test material, wherein each of the at least two measuring capacitors is associated with one of the at least two lead-through openings in such a way that its capacitance is influenceable by a test material situated in the respective lead-through opening. The measuring circuit also contains generator means which are configured to apply at least one electrical alternating signal to the at least two measuring capacitors. The measuring circuit further also contains at least one line for the output of output signals of at least one of the measuring capacitors. The capacitive measuring circuit comprises electrically actuatable selection means, by means of which a true subset of the quantity of all measuring capacitors is selectable in such a way that only the selected subset contributes to the measurement. The set which is complementary to the selected subset shall therefore be dismissed, so that it does not contribute to the measurement.

The selected subset of measuring capacitors preferably contains precisely one measuring capacitor, which is the one into which the test material has been inserted. The terms of "true subset" and "complementary set" shall certainly be understood within the terms of Cantor's set theory: a set B is a true subset of a superset A (B ⊂ A) when each element of B is also contained in A, and when A in addition contains further elements which are not contained in B. The set (A\B) which is complementary to B contains the elements of A which are not contained in B. Furthermore, the selected subset within the terms of the invention shall not be empty, i.e. it shall contain at least one of the measuring capacitors.

In a preferred embodiment, the at least two measuring capacitors are connected in parallel with respect to each other. Each measuring capacitor is associated with a compensation capacitor. The compensation capacitors are designed for compensating influences that disturb the measurement such as local changes in humidity or deformations of the capacitor geometry, but not for receiving test material. The capacitance of each compensation capacitor shall be as large as that of the measuring capacitor to which it is associated. Each measuring capacitor and the respectively associated compensation capacitor preferably form a pair of capacitors which is connected in series. When the measuring capacitor and the compensation capacitor associated with said measuring capacitor are connected in series, the line preferably taps the output signals between the measuring capacitor and the compensation capacitor associated therewith.

Concerning the configuration of the selection means in the measuring circuit in accordance with the invention, the following two embodiments are preferred, which are complementary with respect to each other in a certain way:

(a) According to a first embodiment, the selection means are configured as switches, by means of which an electric connection can be produced and interrupted individually between the at least one alternating signal generator and each of the measuring capacitors. Each measuring capacitor is associated with at least one switch, and all measuring capacitors are connected to a common line for the output of the output signals.

(b) According to a second embodiment, the selection means are configured as multiplexers, by means of which an output signal can be selected which can only originate from the selected subset of the measuring capacitors. All measuring capacitors are connected to the at least one electric alternating signal generator, and each measuring capacitor is associated with an individual line for the output of the respective output signals.

These embodiments can be combined with each other as necessary, despite their complementariness.

The method in accordance with the invention is used for the capacitive analysis of a strand-like test material in a device in accordance with the invention according to one of the preceding claims. The test material is inserted into precisely one of the at least two lead-through openings and is moved through said openings along its longitudinal axis, while there is no test material in the other lead-through openings. The test material influences the capacitance of a measuring capacitor associated with the respective lead-through opening. At least one electrical alternating signal is applied by the generator means to the measuring capacitor associated with the respective lead-through opening. Output signals of at least one of the measuring capacitors are output. A true subset of the set of all measuring capacitors is selected by means of the electrically actuatable selection means in such a way that only the selected subset contributes to the measurement. The set which is complementary to the selected subset is therefore dismissed, so that it does not contribute to the measurement.

In a preferred embodiment, influences that disturb the measurement are compensated by compensation capacitors, each of which is associated with one measuring capacitor.

The method in accordance with the invention also has two preferred embodiments for the selection, which substantially correspond to those of the measuring circuit in accordance with the invention:

(a) The at least one electrical alternating signal is only applied to the selected subset, whereas it is switched off from the set which is complementary to the selected subset. The output signals of all measuring capacitors are output jointly, i.e. on one single common line.

(b) Only the output signals of the selected subset are output, whereas the output signals of the set which is complementary to the selected subset are disregarded. The at least one electrical alternate signal is applied to all measuring capacitors.

A combination of the two embodiments is possible in this case, too.

A number of differences between the invention and the teachings of WO-2005/033697 A1 and U.S. Pat. No. 3,731,069 A are listed below:

WO-2005/033697 A1 and U.S. Pat. No. 3,731,069 A disclose identical lead-through openings. In accordance with the invention however the lead-through openings have different geometrical masses for the different test material diameters.

Measurements are performed on several yarns simultaneously according to WO-2005/033697 A1 and U.S. Pat. No. 3,731,069 A, each of which is moved through a separate lead-through opening. In accordance with the invention, only precisely one test material shall be tested at once. Several lead-through openings are merely provided for the purpose of covering the largest possible diameter range of the test materials.

The capacitive measuring signals are supplied serially or sequentially to a common electronic evaluation system according to WO-2005/033697 A1 and U.S. Pat. No. 3,731,069 A. These sequences are repeated as quickly as possible (often per second) in order to obtain the largest number of measuring data from all yarns. In accordance with the invention however, there is no sequential reading out of measuring signals of the individual measuring capacitors. The selection of the subsets of the measuring capacitors in accordance with the invention is static in the sense that a selection once made remains unchanged during the measurement of a test material. Such a test material should have a length of at least 10 m and the measuring duration on the same test material is at least 10 s for example.

The invention offers a number of advantages over EP-0'924'518 A1, of which a number will be listed below:

Improvement in the sensitivity. The change in the capacitance of the measuring capacitor which is caused by the test material contributes directly to the output signal of the measuring circuit and is not diminished by the other measuring slits which are connected in parallel. In the case of n measuring capacitors of the same capacitance, the sensitivity theoretically increases by the factor n.

Increase in the signal-to-noise ratio. As already explained above, the sensitivity increases. The noise of the measuring circuit remains the same however. As a result, there is an increase in the signal-to-noise ratio by the factor n (with n measuring capacitors of the same capacitance).

Measuring of very thin textile test materials. The higher sensitivity can be used for measuring very fine yarns. This aspect could be especially interesting for chemical fibers.

Reduction in the number of measuring slits. Whereas previously a very thin textile test material had to be measured in a measuring slit with a very low electrode distance, the same test material can now be measured in a wider measuring slit because of the present invention. Due to the higher sensitivity the signal from the wider measuring slit can still be sufficient.

Reduction in the generator voltage. The higher sensitivity may also allow operating the measuring circuit with a lower generator voltage. This leads to a reduction in the consumed power and therefore to lower heating. Furthermore, more components which meet the requirements of the output stage and are less expensive are available for implementing the measuring circuit.

Reduction in the load capacitance. The present invention reduces the total capacitance of the measuring circuit. As a result, the active output stage is subject to a lower load, is heated to a lower extent and shows a lower tendency to disturbing oscillations.

Improvement in the dust accumulation problem. Certain yarns can develop a high amount of dust especially at high draw-off speeds. It accumulates in the currently used measuring slit, but also in the other measuring slits, which leads to a drift in the output signal. This drift is reduced by the present invention in such a way that the measuring slits which are not currently used no longer have an influence on the output signal any more.

DRAWINGS

Preferred embodiments of the invention will be explained in closer detail below by reference to the drawings. FIG. 2 also shows the state of the art for comparison purposes.

DESCRIPTION

Figure 3:
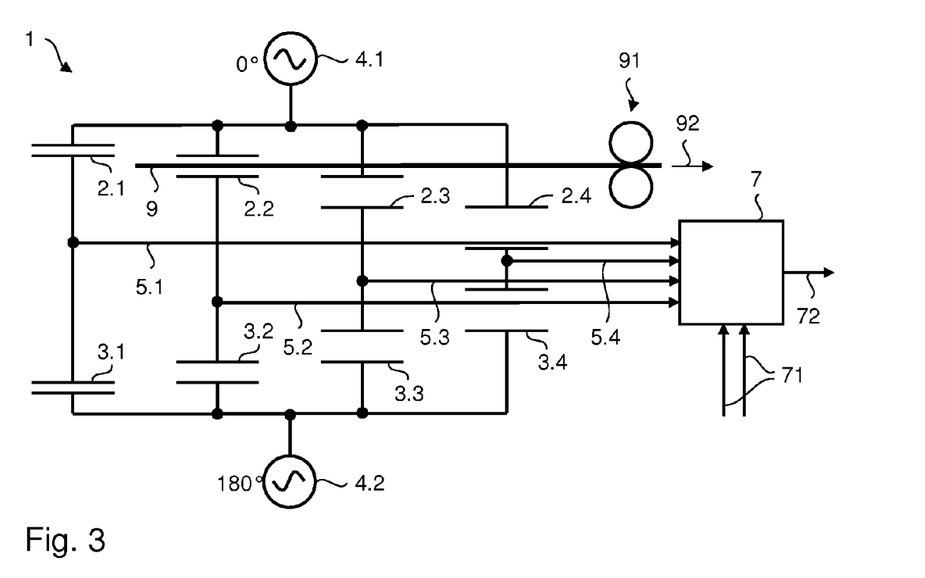
FIGS. 3-5 show three embodiments of a measuring circuit in accordance with the invention.

FIG. 3 shows a circuit diagram of a first embodiment of the measuring circuit 1 in accordance with the invention. Said measuring circuit 1 comprises four measuring capacitors 2.1-2.4 which can be configured as flat plate capacitors. Each of the measuring capacitors 2.1-2.4 is associated with a lead-through opening 102.1-102.4, as shown in FIG. 1 for example. The electrodes 103.1, 103.2 shown in FIG. 1 could be the electrodes of the measuring capacitor 2.2 of FIG. 3 for example. In accordance with the differently wide lead-through openings 102.1-102.4, the respectively associated measuring capacitors 2.1-2.4 have different electrode distances. As is indicated in FIG. 3, the lead-through openings or measuring capacitors 2.1-2.4 are mutually arranged in such a way that a textile test material 9 can be inserted into precisely one measuring capacitor 2.2. For this purpose, the measuring capacitors 2.1-2.4 are mutually offset in the direction transversely to their capacitor plates. An offset in the direction parallel to the capacitor plates is not necessary and only shown in FIG. 3 in order to provide the elements of the measuring circuit 1 with more clarity in the illustration.

The textile test material 9 is moved during the measurement along its longitudinal direction through precisely one of the measuring capacitors 2.1-2.4. In the example of FIG. 3, this is the second measuring capacitor 2.2. The movement of the test material 9 is generated by a conveying mechanism 91, and the direction of movement is indicated with an arrow 92. The conveying mechanism can be configured in the known manner as a roller delivery device with two mutually cooperating conveying rollers, of which at least one is driven for rotation. The conveying mechanism 91 is configured for conveying precisely one test material 9 by precisely one selected 102.2 of all lead-through openings 102.1-102.4.

The measuring circuit 1 further comprises four compensation capacitors 3.1-3.4, which are each associated with a measuring capacitor 2.1-2.4 and form a capacitor pair with it. A measuring capacitor 2.1 and the associated compensation capacitor 3.1 should have the same capacitance if possible and are connected in series. The capacitances of the measuring capacitors 2.1-2.4 can be equal among each other or different from each other. The measuring capacitors 2.1-2.4 are configured for receiving an elongated textile test material 9 such as a yarn; the compensation capacitors 3.1-3.4 are not configured in this way.

Alternating signal generators 4.1, 4.2 apply two electrical alternating signals, which are anti-symmetrical with respect to each other, to the capacitor pairs 2.1, 3.1 to 2.4, 3.4. This means that the differences of the two applied alternating signals to a constant reference signal are equal with respect to amount and phase-shifted by 180° with respect to each other. It is possible to use one single alternating signal generator or several alternating signal generators 4.1, 4.2. The at least one alternating signal generator 4.1, 4.2 can be configured as an LC oscillator (as described in EP-0'924'518 A1), which forms an electric oscillating circuit together with the elements 2.1-2.4, 3.1-3.4 of the measuring circuit 1. Alternatively, elements 2.1-2.4, 3.1-3.4 of the measuring circuit 1 can be decoupled from the at least one alternating signal generator 4.1, 4.2 in such a way that they do not relevantly influence parameters of the electrical alternating signal generated by the at least one alternating signal generator 4.1, 4.2, as described in WO-2010/043064 A1. In the latter case, the at least one alternating signal generator 4.1, 4.2 is preferably configured as a synthesizer, i.e. as a mixed-signal (digital and analog) electrical device for generating analog electrical alternating voltage signals. A direct digital synthesizer (DDS) is used in a highly advantageous manner. As a result, parameters of the electrical alternating signal (e.g. its fundamental frequency) can be chosen freely.

In contrast to the state of the art according to FIG. 2, the output signals of the individual capacitor pairs 2.1, 3.1 to 2.4, 3.4 are tapped individually in FIG. 3. The tapping respectively occurs on lines 5.1-5.4 between the measuring capacitor 2.1-2.4 and the associated compensation capacitor 3.1-3.4. The four lines 5.1-5.4 open into a multiplexer 7, which selects a single line 5.2 from these lines and outputs its signal on an output line 72. The multiplexer 7 can be configured as an analog high-frequency multiplexer. One or several control signals 71 inform the multiplexer 7 which of the lines 5.1-5.4 or which output signal is to be selected. The control signals 71 can be supplied by a generally known, preferably digital (not shown) driver component. As is known from the state of the art, the output signal can be processed (e.g. amplified, filtered and/or converted) before or after the multiplexer 7. Individual switches which connect the capacitor pairs 2.1, 3.1 to 2.4, 3.4 to a common line can be provided instead of the multiplexer 7 (see FIG. 5).

The following table compares the properties of circuits 1', 1 according to FIGS. 2 and 3 with each other. The following assumptions are made:
- The alternating voltages applied by the alternating signal generators 4.1', 4.2' and 4.1, 4.2 against ground are $U_\pm = \pm \frac{1}{2} U_0 \sin \omega t$, wherein $U_0$ is a voltage amplitude, $\omega$ an angular frequency and t the time.
- The test material 9' and 9 is situated for example in the second measuring capacitor 2.2' and 2.2, respectively, which has the capacitance $C_2$.
- U is the tapped output voltage against ground.
- All capacitors 2.1'-2.4', 3.1'-3.4' and 2.1-2.4, 3.1-3.4 have the same capacitance C without the test material.
- The relative change in capacitance $$\left|\frac{\Delta C_2}{C_2}\right|$$

caused by the test material 9' and 9 is small, e.g. <0.1, so that the linear approximation $$\Delta U \approx \frac{\partial U}{\partial C_2} \Delta C_2$$

can be used.
- Parasitic capacitances are disregarded.

|  | State of the art (FIG. 2) | Invention (FIG. 3) |
|---|---|---|
| Total capacitance $C_{tot}$ | $\dfrac{4C(C_2 + 3C)}{C_2 + 7C}$ | $\dfrac{C_2 C}{C_2 + C}$ |
| $C_{tot}(C_2 = C)$ | $2C$ | $\dfrac{C}{2}$ |
| Output voltage U | $\dfrac{U_0}{2} \cdot \dfrac{C_2 - C}{C_2 + 7C}$ | $\dfrac{U_0}{2} \cdot \dfrac{C_2 - C}{C_2 + C}$ |
| $U(C_2 = C)$ | 0 | 0 |
| Sensitivity $\dfrac{\partial U}{\partial C_2}$ | $U_0 \dfrac{4C}{(C_2 + 7C)^2}$ | $U_0 \dfrac{C}{(C_2 + C)^2}$ |
| $\left.\dfrac{\partial U}{\partial C_2}\right|_{C_2 = C}$ | $\dfrac{U_0}{16C}$ | $\dfrac{U_0}{4C}$ |

The table shows that the measuring circuit 1 in accordance with the invention has a total capacitance $C_{tot}$ (without the alternating signal generators 4.1, 4.2) which is four times lower and a sensitivity $$\left.\frac{\partial U}{\partial C_2}\right|_{C_2 = C}$$

which is four times higher than the measuring circuit 1' according to the state of the art. The advantages of the invention as described above are the result of this increase in the sensitivity by the factor n=4.

The selection of a single measuring capacitor 2.2 represents a special case of the situation in which a number m (1≤m<n) of measuring capacitors is selected. In the general case, the sensitivity is increased by the factor $$\frac{n}{m}.$$

These theoretical statements have partly already been confirmed in experiments, wherein the experimental results were slightly worse than the theoretical predictions due to parasitic capacitances. The practical benefits of the invention are evident however. The selection of more than one measuring capacitor could be advantageous in order to achieve purposeful damping of the output signal, e.g. in the case of a test material of large mass density or high dielectric constant.

Figure 4:
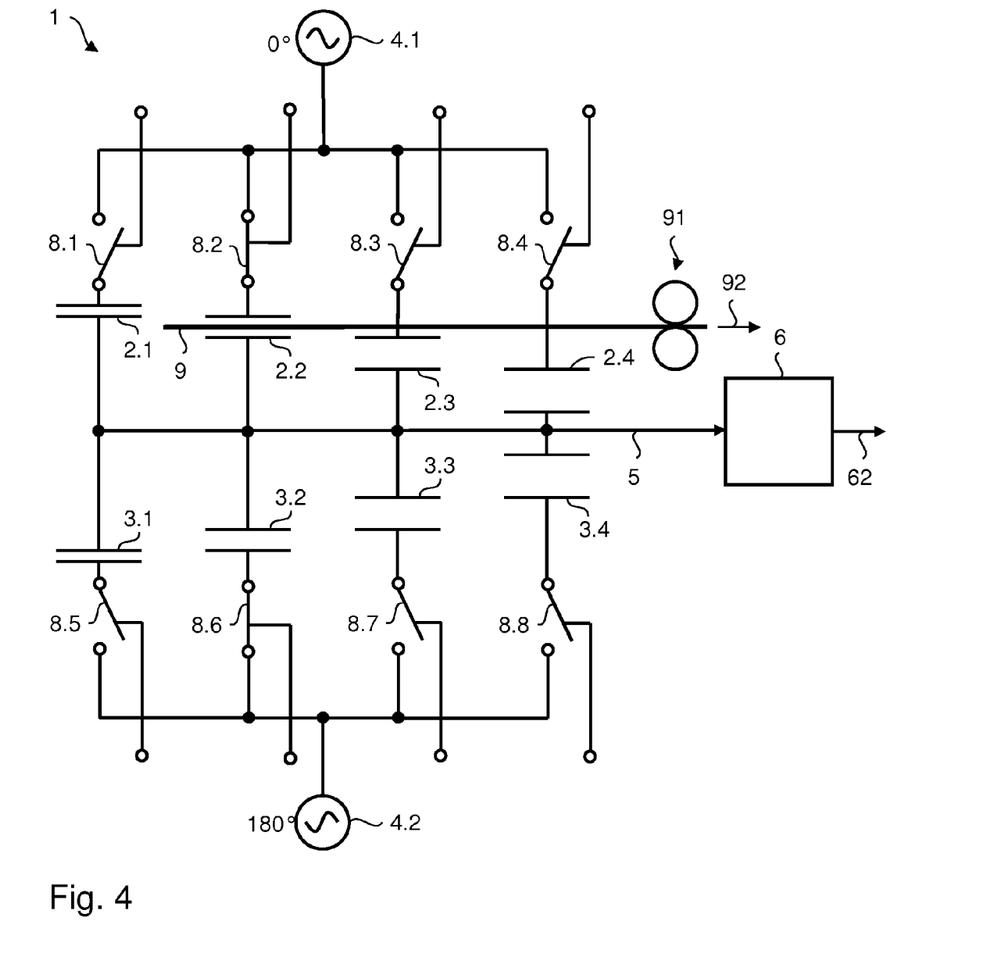

FIG. 4 shows a second embodiment of the measuring circuit 1 in accordance with the invention, which also comprises four capacitor pairs 2.1, 3.1 to 2.4, 3.4. In this case, the electric connections between the capacitor pairs 2.1, 3.1 to 2.4, 3.4 and the alternating signal generators 4.1, 4.2 can be interrupted and established individually. This is carried out by switches 8.1-8.8 which are switched by respective, preferably digital, control signals. These switches 8.1-8.8 can be configured as relays or as analog semiconductor switches. The switch pair 8.1, 8.5 which is associated with a capacitor pair 2.1, 3.1 is preferably coupled in such a way that it is switched in parallel, i.e. the two switches 8.1, 8.5 are either both open or both closed. The control signals can be supplied by a known, preferably digital driver component (not shown). In order to benefit from the compensation and to operate the measuring circuit 1 at the operating point U=0, the switches 8.2, 8.6 associated with a capacitor pair 2.2, 3.2 should either both be open or both be closed. The best advantages are obtained when precisely one capacitor pair 2.2, 3.2 (e.g. the second capacitor pair) is connected to the alternating signal generators 4.1, 4.2 and all other capacitor pairs 2.1, 3.1; 2.3, 3.3; 2.4, 3.4 are separated from the alternating signal generators 4.1, 4.2. In this second embodiment one single line 5 can connect all capacitor pairs 2.1, 3.1 to 2.4, 3.4 to the signal processing unit 6, as is the case in the state of the art. A multiplexer is not required in this case.

There is a kind of complementarity between the embodiments of FIGS. 3 and 4. In the first embodiment, all capacitor pairs 2.1, 3.1 to 2.4, 3.4 remain connected to the alternating signal generators 4.1, 4.2; in return, only the line 5.2 associated with the measuring capacitor 2.2 loaded with the test material 9 is activated for output signals, whereas the other lines 5.1, 5.3, 5.4 are deactivated. In the second embodiment, only the one capacitor pair 2.2, 3.2 is connected to the alternating signal generators 4.1, 4.2 whose measuring capacitor 2.2 is loaded with the test material 9, whereas the other capacitor pairs 2.1, 3.1; 2.3, 3.3; 2.4, 3.4 are switched off; in return, all capacitor pairs 2.1, 3.1 to 2.4, 3.4 remain connected to the common line 5 for the output signals.

Figure 5:
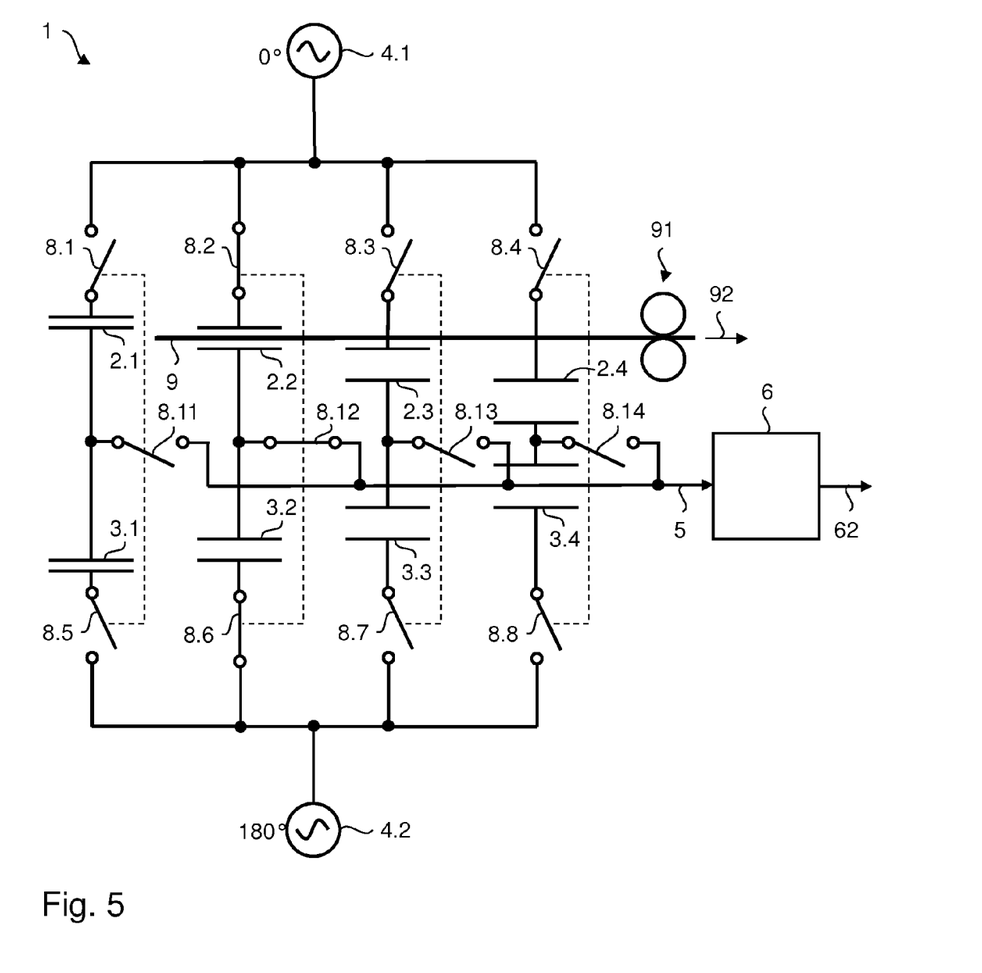

FIG. 5 shows a third embodiment of the measuring circuit 1 in accordance with the invention. This third embodiment represents a combination of the embodiments of FIGS. 3 and 4. Both switches 8.11-8.14 between the capacitor pairs 2.1, 3.1 to 2.4, 3.4 and the common line 5 and also switches 8.1-8.8 between the alternating signal generators 4.1, 4.2 and the capacitor pairs 2.1, 3.1 to 2.4, 3.4 are provided. The switch triplet 8.1, 8.5, 8.11 associated with a capacitor pair 2.1, 3.1 is preferably coupled in such a way that it is switched in parallel, i.e. the three switches 8.1, 8.5, 8.11 are either all open or all closed. This is shown in FIG. 5 by dashed lines. The switches 8.1-8.8, 8.11-8.14 can be configured for example as relays or as analog semiconductor switches. Due to the double separation of the non-selected capacitor pairs 2.1, 3.1; 2.3, 3.3; 2.4, 3.4, parasitic couplings, the load capacitance and the output capacitance are reduced, which can be especially advantageous.

The measuring circuit 1 in accordance with the invention may contain calibration means for zero calibration without test material. Such calibration means are known for example from the specifications EP-0'924'518 A1, WO-2010/043063 A1 and WO-2010/043065 A1. The calibration means are not shown in the drawings for reasons of simplicity of the illustration.

It is understood that of the present invention is not limited to the embodiments as discussed above. The person skilled in the art will be able to derive further variances with knowledge of the invention which also belong to the subject matter of the present invention.

REFERENCE NUMERALS

1 Measuring circuit
2.1-2.4 Measuring capacitors
20' Half bridge branch
3.1-3.4 Compensation capacitors
30' Half bridge branch
4.1, 4.2 Alternating signal generators
5, 5.1-5.4 Lines for output signals
6 Signal processing unit
62 Output line
7 Multiplexer
71 Control signals
72 Output line
8.1-8.8, 8.11-8.14 Switch
9 Test material
91 Conveying mechanism
92 Direction of movement of the test material
101.1-101.5 Carrier plates
102.1-102.4 Measuring gap
103.1, 103.2 Capacitor electrodes
104.1, 104.2 Electric lines

The invention claimed is:

1. A device for taking a capacitive measurement of a moving strand of test material, the device comprising:
    lead-through openings, each with different geometrical masses, disposed such that the test material is movable along a longitudinal axis through only a selected one of the openings,
    a conveyor for conveying only one strand of test material through only the selected one of the openings, and
    a capacitive measuring circuit, comprising,
        measuring capacitors associated with the openings such that a capacitance of a given measuring capacitor is influenced by the test material in an associated opening,
        a generator for applying an electrical alternating signal to the measuring capacitors,
        at least one line for carrying output signals from the measuring capacitors, and
        and electrically actuatable selector, for selecting a subset of the measuring capacitors, such that only the selected subset contributes to the measurement.

2. The device of claim 1, wherein each measuring capacitor is associated with a compensation capacitor for compensating influences that disturb the measurement, and wherein each measuring capacitor and the compensation capacitor associated therewith form a capacitor pair connected in series.

3. The device of claim 2, wherein a given one of the lines taps the output signal between the measuring capacitor and the compensation capacitor that form the associated capacitor pair.

4. The device of claim 1, wherein the selector comprises switches for individually establishing and interrupting electrical connections between the generator and each of the measuring capacitors.

5. The device of claim 4, wherein:
    the generator applies equally large anti-phase electrical alternating signals to the measuring capacitors and the compensation capacitors, respectively, and
    the selector comprises switches for individually establishing and interrupting electrical connections between the generator and each of the compensation capacitors.

6. The device of claim 4, wherein at least one switch is associated with each measuring capacitor, and all measuring capacitors are connectable to a common line for the output of output signals.

7. The device of claim 6, wherein the selector comprises switches for individually establishing and interrupting electrical connections between the common line and each of the measuring capacitors.

8. The device of claim 1, wherein each measuring capacitor is associated with an individual line for the output of its output signals, and the selector comprises multiplexers for selecting only those output signals that originate from the selected subset of the measuring capacitors.

9. A method for taking a capacitive measurement of a moving strand of test material, comprising:
    inserting the test material into only a selected one of a plurality of lead-through openings and moving the test material through the selected opening along a longitudinal axis, with no test material disposed in the non-selected lead-through openings, the test material thereby influencing a capacitance of a measuring capacitor associated with the selected lead-through opening, applying an electrical alternating signal with a generator to the measuring capacitor associated with the selected lead-through opening, outputting output signals produced by the measuring capacitor, and selecting a subset of the measuring capacitors with the electrically actuatable selection means such that only the selected subset of measuring capacitors contributes to the measurement.

10. The method of claim 9, further comprising compensating for influences that disturb the measurement with compensation capacitors, each of which is associated with a measuring capacitor.

11. The method of claim 9, wherein the electrical alternating signal is applied to the selected subset of measuring capacitors and not applied to the non-selected measuring capacitors.

12. The method of claim 11, wherein the output signals of all measuring capacitors are output jointly.

13. The method of claim 11, wherein the electrical alternating signal is applied to the selected subset of measuring capacitors and not applied the non-selected measuring capacitors, and the output signals of the selected subset of measuring capacitors are output and the output signals of the non-selected measuring capacitors are disregarded.

14. The method of claim 13, wherein the electrical alternating signal is applied to all of the measuring capacitors and only the output signals of the selected subset of measuring capacitors are output.

15. The method of claim 9, wherein the output signals of the selected subset of measuring capacitors are output and the output signals of the non-selected measuring capacitors are disregarded.

* * * * *